United States Patent [19]

Brown, III

[11] 4,242,448

[45] Dec. 30, 1980

[54] REGENERATION OF SCRUBBER EFFLUENT CONTAINING SULFATE RADICALS

[76] Inventor: Robert S. Brown, III, 9726 Cedar Dr., Shawnee Mission, Kans. 66207

[21] Appl. No.: 29,272

[22] Filed: Apr. 12, 1979

[51] Int. Cl.$^3$ .................... C12P 39/00; C12P 3/00; C10G 32/00
[52] U.S. Cl. .................... 435/42; 435/266; 435/281; 435/282; 435/168; 55/73
[58] Field of Search ................ 435/42, 168, 266, 281, 435/282

[56] References Cited

U.S. PATENT DOCUMENTS

| | | | |
|---|---|---|---|
| 1,701,825 | 2/1929 | Seil | 435/266 |
| 1,763,641 | 4/1930 | Beckman | 435/266 |
| 1,813,882 | 7/1931 | Behm | 435/248 |
| 2,056,668 | 10/1936 | Bavin et al. | 435/136 |
| 2,228,628 | 1/1941 | Hahn | 435/161 |
| 2,367,803 | 1/1945 | Schindler | 196/23 |
| 2,382,010 | 8/1945 | Hodges | 210/2 |
| 2,413,278 | 12/1946 | Zobell | 195/1 |
| 2,521,761 | 9/1950 | Strawinski | 435/282 |
| 2,574,070 | 11/1951 | Strawinski | 435/282 |
| 2,641,564 | 6/1953 | Zobell | 435/282 |
| 2,765,217 | 10/1956 | Conroy, Jr. et al. | 23/225 |
| 2,807,570 | 9/1957 | Updegraff | 166/246 |
| 2,897,148 | 7/1959 | Laboureur | 435/251 |
| 2,975,103 | 3/1961 | Kirshenbaum | 435/282 |
| 3,020,205 | 2/1962 | Jensen | 435/168 |
| 3,105,014 | 9/1963 | Harrison | 166/246 |
| 3,720,606 | 3/1973 | Horney et al. | 210/11 |
| 3,737,374 | 6/1973 | Stern et al. | 435/145 |
| 4,124,501 | 11/1978 | Yen et al. | 435/281 X |

OTHER PUBLICATIONS

Bergey's Manual of Determinative Bacteriology, 8th Edition 1974, pp. 112-115,418-421.

*Primary Examiner*—Lionel M. Shapiro
*Attorney, Agent, or Firm*—Fishburn, Gold and Litman

[57] ABSTRACT

Stack gases from fossil fuel burning operations before being released to the atmosphere are passed through a scrubber, wherein sulfur dioxide is removed from the gases by scrubbing with metallic carbonates. The metallic carbonates react with the sulfur dioxide to form a liquid effluent comprising metallic sulfates. The effluent is placed in a basin and inoculated with a microorganism which reduces sulfate ions to hydrogen sulfide, preferably bacteria from the genus Desulfovibrio, thereby also regenerating metallic carbonates. The effluent is contemporaneously or serially inoculated with saline compatible bacteria from the genus Beggiatoa whereby the hydrogen sulfide is oxidized to form sulfur. After treatment by the bacteria, the effluent is recycled to the scrubber for use therein and the sulfur is recovered.

9 Claims, No Drawings

REGENERATION OF SCRUBBER EFFLUENT CONTAINING SULFATE RADICALS

BACKGROUND OF THE INVENTION

Most fossil fuels, such as crude oil, blue water gas, carbureted water gas, and in particular coal, have varying amounts of sulfur contained therein. When burned in the presence of oxygen, sulfur dioxide is formed. The sulfur dioxide is a noxious gas and, if released into the ambient air, combines with water to form destructive sulfurous acid. As an example, a 650,000 KW power plant burning coal with a 3% sulfur content will generate about 39,000 pounds of sulfur dioxide per hour. To avoid severely polluting the atmosphere, this sulfur dioxide must be removed from the stack or exhaust gases. The sulfur dioxide becomes a particularly troublesome problem, since shortage of crude oil has increased the use of coal having higher percentages of sulfur therein.

One somewhat effective method of removing sulfur dioxide from stack gases is to pass the gas through scrubber wherein the sulfur dioxide is reacted with an inorganic alkaline substance to form a non-gaseous sulfur compound which exits the scrubber with the liquid effluent therefrom. Such scrubbers include spray towers, packed towers, fluid bed reactors, etc.

A wide variety of inorganic alkaline materials have been used to form the scrubbing liquid. Aqueous solutions comprising at least one of the metallic carbonates of calcium, magnesium and sodium have been especially popular. These metallic carbonates react with the sulfur dioxide to form carbon dioxide and metallic sulfite. The metallic sulfite is normally oxidized to a metallic sulfate by the excess oxygen remaining in the stack gases after the fuel burning operations. Functionally, a metallic carbonate, which is highly soluble in the aqueous scrubber solution and which also reacts to form a highly soluble metallic sulfate (sulfite), is preferred for use in the scrubber. The carbonates and sulfates of sodium and especially magnesium have high relative solubility, but are somewhat short in supply and substantially more expensive as compared to the less soluble calcium carbonates and sulfates. Thus, in the past calcium carbonate has been extensively used in scrubbers because of the large supply, relatively lower cost, and because the scrubber effluent can be safely disposed of since the calcium sulfate (gypsum) therein is relatively innocuous to the environment.

Unfortunately calcium carbonates and sulfates require extreme care with regard to scrubber operational parameters, such as temperature and pH control. Slight variations cause heavy scaling of the scrubber and even optimum control conditions often result in some scaling, thereby requiring eventual shut-down and cleaning of the scrubber internal structure. In addition, due to changes in environmental law, expense and public opinion, it is becoming impractical to land-fill large amounts of scrubber effluent sludge material. It is estimated that as much as 18 million tons of scrubber sludge is produced in the United States per year, substantially all of which must be land-filled under present scrubber processes.

OBJECTS OF THE INVENTION

Therefore, the principal objects of the present invention are: to provide a method for regenerating sulfur dioxide scrubber effluent having therein non-gaseous inorganic sulfur compounds, whereby the effluent can be reused in the scrubber; to provide such a method which makes use of highly soluble and non-scaling scrubber reactants, such as magnesium carbonate; practical; to provide such a method which uses a first microorganism, preferably bacteria from the genus Desulfovibrio, to reduce the inorganic sulfur compounds, especially metallic sulfates, to hydrogen sulfide to thereby regenerate the effluent solution; to provide such a method wherein a second microorganism, preferably a bacteria which is saline compatible with the Desulfovibrio from the genus Beggiatoa, is used to remove the hydrogen sulfide from the effluent solution and produce elemental sulfur therefrom, thus rendering the hydrogen sulfide environmentally safe; to provide such a method wherein both anaerobic Desulfovibrio and aerobic Beggiatoa can act contemporaneously or serially on the effluent to regenerate same; and to provide such a method which reduces the expense of scrubbing sulfur dioxide, makes the scrubbing process easier to operate, reduces scrubber sludge waste production and is particularly well adapted for the proposed use thereof.

Other objects and advantages of this invention will become apparent from the following description wherein are set forth, by way of example, certain embodiments of this invention.

SUMMARY OF THE INVENTION

In general the present invention comprises a process for regenerating sulfur containing sludge effluent from a fossil fuel power generation plant scrubber into a reusable solution capable of oxidizing and degassifying sulfur containing compounds, especially sulfur dioxide, in the scrubber. The sludge effluent is placed in a holding basin after exiting the scrubber. The generally inorganic sulfur containing compounds in the sludge, in particular metallic sulfates, are innoculated or otherwise treated, with a sulfur reducing microorganism which produces hydrogen sulfide from the sulfur in the sludge. Preferably the sulfur reducing microorganism is a bacteria from the genus Desulfovibrio, including the species *vulgaris, salexigens, africanus, gigas,* and *desulfuricans.* The effluent, having hydrogen sulfide therein, is also innoculated or otherwise treated with a microorganism which oxidizes the hydrogen sulfide and preferably forms elemental sulfur, which sulfur is periodically harvested from the basin. A preferred oxidizing microorganism is a bacteria from the genus Beggiatoa, including the species *arachnoida, gigantea, leptomitiformis, minima, mirablis* and *alba*. While the above described sulfur reduction and oxidation can occur in separate portions of the basin or even in separate isolated basins, it is preferred that the two microorganisms be present in the same portion of the basin, except at different layers therein, and that the sulfur reduction and oxidation occur substantially contemporaneously, thereby lessening the opportunity for the hydrogen sulfide to escape into the ambient temperature. A particularly suitable combination of microorganisms has been found to be *Desulfovibrio desulfuricans* and *Beggiatoa alba*. These two bacteria have been found to be surprisingly compatible even though the former is anaerobic and the latter is aerobic, if sufficient oxygen is supplied to the basin to meet the aerobic requirement.

DETAILED DESCRIPTION OF THE PREFERRED EMBODIMENT

As required, detailed embodiments of the present invention are disclosed herein; however, it is to be understood that the disclosed embodiments are merely exemplary of the invention which may be embodied in various forms. Therefore, specific method or process details disclosed herein are not to be interpreted as limiting, but merely as a basis for the claims and as a representative basis for teaching one skilled in the art to variously employ the present invention in virtually any appropriately detailed method or process.

In the present embodiment, a coal fired boiler is provided with a conventional stack gas scrubber vessel wherein gaseous sulfur compounds formed by oxidation of sulfur contained in the burning coal are substantially removed from the stack gas by reaction with a chemical reactant scrubbing solution therein. Normally, the stack or exhaust gas comprises sulfur dioxide (the most frequent gaseous sulfur compound oxidized during combustion of the coal), carbon dioxide, oxygen, nitrogen, and various other combustion products. The chemical reactants in the scrubbing solution of the scrubber in the present embodiment comprises an aqueous mixture of magnesium oxide and/or magnesium carbonate. Normally, any magnesium oxide reacts quickly with the carbon dioxide in the stack gas to form magnesium carbonate. As will be discussed later, the influent scrubber solution may also contain magnesium sulfate, bacteria, and other products of the regeneration process. In normal operation the magnesium carbonate in the scrubber solution is injected contemporaneously with and reacts with the sulfur dioxide in the stack gas thereby forming magnesium sulfite. The magnesium sulfite is readily oxidized by the oxygen present in the stack gas thereby forming magnesium sulfate which is non-gaseous and substantially water soluble. Thus, the gaseous and noxious sulfur dioxide is converted to non-gaseous and non-noxious magnesium sulfate which exits the scrubber along with the scrubber solution effluent. Because of side and incomplete reactions, other sulfur containing compounds, including thiosulfate radicals, hyposulfite radicals, bisulfate radicals, sulfide radicals, and various intermediate radicals thereof, may also be present in the scrubber solution effluent. As used herein the term "radical" means a portion of a molecule, whether as ion in solution or part of a unitary molecule, and includes such terms as moiety and ion; also "radical" may be comprised of a single atom or a group of atoms.

In the preferred embodiment, magnesium carbonate has been chosen as the scrubber solution chemical reactant or active medium by which the gaseous sulfur compounds are removed from the stack gas. Magnesium carbonate, as well as magnesium sulfate, are relatively highly soluble in water and cause little or no scaling in the scrubber and associated processing equipment. The regeneration process, according to the present invention, functions well in the presence of the various aforementioned magnesium salts. It is foreseen that any compound suitable for reacting with the gaseous sulfur dioxide and producing a non-gaseous compound therefrom would be suitable as the scrubber solution active medium. It has been found that metallic carbonates which exhibit at least some water solubility and are reactive with the sulfur dioxide meet this criteria. Many conventional processes have used a carbonate (or oxide which converts to a carbonate in the presence of carbon dioxide) of calcium, sodium, or magnesium for this purpose. Calcium carbonate has historically been preferred, since it is relatively more abundant and less expensive than the sodium or magnesium carbonates. Calcium carbonate thus has an economic advantage especially in processes where large quantities of the scrubber effluent are scrapped, as in a land-fill. However, the more water soluble magnesium carbonate is preferably used herein. The magnesium salt is economically justified under the present process, since it is recycled and there are substantially fewer control problems and less clean-up associated therewith, as compared to the calcium salt. Although magnesium carbonate is preferred, other chemical reactants which function to degassify the sulfur dioxide in the stack gas, as described above, will work with the present process.

The liquid scrubber effluent comprising reducible sulfur compounds, in particular magnesium sulfate in an aqueous solution, along with any unused magnesium carbonate, is conveyed, as by pumps and suitable piping, to a basin. In the present embodiment, the basin comprises a large holding pond. The size of the pond is dependent upon the periodic quantity of sulfur dioxide released by the coal burning and several other factors which will be discussed hereinafter. It is foreseen that the basin could be one or more enclosed tanks, one large pond, or a number of smaller ponds connected in series. Since an aerobic bacteria is utilized in the present embodiment, it is necessary that the basin have sufficient oxygen therein to supply the requirements of the aerobic bacteria. When the basin is enclosed, oxygen may be bubbled or otherwise mechanically added to the scrubber effluent before or while in the basin. When the basin has an open top, oxygen may be taken directly from the air by the aerobic bacteria near the surface, however, care must be taken not to substantially "turn over" the liquid layers or strata in such a basin, thereby placing the aerobic bacteria too far from the surface, thus reducing the oxygen supply thereof and killing same. Preferably the basin is baffled or otherwise aligned such that the residence time of the scrubber effluent between entry and exit from the basin is maximized and such that each increment of scrubber effluent has approximately an equal residence time within the basin The microorganisms of the present embodiment comprise a first bacteria which reduces the sulfur in the reducible sulfur compounds (generally sulfate radicals) contained in the scrubber effluent, thereby producing hydrogen sulfide and a second bacteria which oxidizes the sulfur in the hydrogen sulfide to a non-gaseous and non-noxious state, preferably elemental sulfur. Although the first and second bacteria may be serially applied to the scrubber effluent, it is preferable to inoculate the effluent with both bacteria contemporaneously. In this manner there is less likelihood that the hydrogen sulfide produced by the first bacteria will escape into the ambient atmosphere before the second bacteria can oxidize the sulfur in the hydrogen sulfide. As an added precaution against release of noxious hydrogen sulfide into the air, the basin may be enclosed or, alternatively, covered with a thin layer of suitable plastic which will float on the surface of the scrubber effluent in the basin and be substantially impermeable to hydrogen sulfide. A suitable first sulfur reducing bacteria may be chosen from the genus Desulfovibrio, especially the species *desulfuricans, vlugaris, salexigens, africanus* and *gigas*. A suitable second (sulfur oxidizing)

bacteria may be chosen from the genus Beggiatoa, especially the species *alba, arachnoida, gigantea, leptomitiformis, minima* and *mirabilis*. It is forseen that other species of bacteria which function equivalently may be substituted for the above. The bacteria chosen must be saline compatible or, alternatively, have no functional preference for or against salt. In the present embodiment the first bacteria is *Desulfovibrio desulfuricans* and the second bacteria is *Beggiatoa alba,* these bacteria being anaerobic and aerobic respectively. Preferably both bacteria are used in the basin, being separated or stratified therewithin. The *Desulfovibrio desulfuricans,* although anaerobic, has slight tolerance to oxygen. However, it prefers the bottom of a basin or pond and functions well at that stratum. The *Beggiatoa alba* is aerobic and must have oxygen to support same and normally lives in a stratum near the surface where oxygen is more readily available. It is therefore important that the pond be sufficiently stable to prevent the strata, especially the upper stratum with the aerobic bacteria from being mixed, whereby the aerobic bacteria would be placed in an oxygen deficient stratum and die. In certain instances a mechanical aerator may be required to insure that sufficient oxygen is supplied to the pond to support the *Biggiatoa alba*. Should a plastic cover be used on the pond air must normally be fed thereunder or some other suitable means provided to oxygenate the scrubber effluent and thereby support the aerobic bacteria.

According to the present embodiment, it has been found that, surprisingly, the *Desulfovibrio desulfuricans* and the *Beggiatoa alba* survive well in the same solution even though they are anaerobic and aerobic respectively, especially in a pond or basin wherein they can reside in somewhat separate strata therein. In fact the manner in which each of the above bacteria affects the pond environment seems to enhance the other. That is, the *desulfuricans* produces hydrogen sulfide upon which the *alba* thrives and the *alba* removes the hydrogen sulfide from the solution which seems to enhance the activity and growth of the *desulfuricans*. Also since each bacteria is in a separate stratum, there is less likelihood of interbacteria cannibalism. Thus both of these bacteria cooperate well in a somewhat unusual and normally hostile environment.

Each type of bacteria has special optimum conditions under which it grows and thrives and which are sometimes required for survival depending on the particular species of bacteria. In addition to the above mentioned conditions of salinity and oxygen dependence, bacteria must have a source of carbon to survive. In the present embodiment the scrubber effluent pond is very inhospitable to most animal or vegetable life, because of the hydrogen sulfide, thus there are few natural organic sources of carbon therein. Therefore, it is necessary to supplement the carbon supply in the pond. This may be accomplished by adding any bacteria compatible hydrocarbon such as sugar, crude oil, or the like.

Most bacteria have a higher rate of metabolism as the temperature raises and thus perform better under the present invention in comparatively warmer ponds. However, both of the bacteria of the present invention are found as far north as Alaska and throughout the warmer climates. Since it is often important to limit pond size, since the pond size is somewhat determined by the scrubber effluent regeneration speed of the bacteria and since regeneration speed is slowest when the pond is at its yearly minimum temperature, it is therefore important to size the pond to regenerate sufficient magnesium carbonate during the coldest periods of the year. Generally it is beneficial to keep the pond temperature as high as possible without getting so warm as to kill the bacteria. This may be accomplished by using the scrubber effluent pond as part of a heat sink for the turbine in a coal fired power plant.

The size of the pond is therefore dependent on several factors. The total volume of the pond is related to the size of the power plant and maximum amount of sulfur in the coal being used. In the present embodiment there must be sufficient magnesium carbonate to react with the hourly flow rate of sulfur dioxide into the scrubber over the number of hours required for the bacteria to regenerate magnesium carbonate (magnesium oxide) from the magnesium sulfate during the coldest part of the year. At an average pond temperature in the nature of 70 to 80 degrees Fahrenheit (° F.), regeneration of magnesium carbonate from magnesium sulfate using the bacteria of the present invention was found to occur in about 30 days. Thus at such a minimal temperature, a pond requires a volume in the nature of 30 times the daily average scrubber discharge rate. The pond should be at least 4 feed deep to allow stratification of the bacteria. The bacteria stratum appears to widen as the pond deepens, especially the anaerobic bacteria stratum. In the present embodiment a pond 10 to 30 feet deep is preferred.

According to the present embodiment, magnesium sulfate dissociates in the pond to form free sulfate radicals therein. The sulfur in the sulfate radicals is reduced to hydrogen sulfide by the *Desulfovibrio desulfuricans* bacteria. At this time it is believed that the magnesium associates with an oxygen radical thereby forming magnesium oxide. If there is any carbon dioxide present in the pond, and there normally is, the magnesium oxide associates therewith and becomes magnesium carbonate. If no or insufficient carbon dioxide is in the pond, this association reaction occurs in the scrubber where large amounts of carbon dioxide are present in the coal combustion gasses (stack gas). Hydrogen sulfide is normally produced by the *Desulfovibrio desulfuricans* near the bottom stratum of the pond and diffuses therethrough to stratum having the *Beggiatoa alba* therein, whereupon the hydrogen sulfide is oxidized by the bacteria. It is believed that the *Beggiatoa alba* ingest the hydrogen sulfide and oxidize the sulfur therein to an elemental state. The elemental sulfur is stored in pockets in the *Beggiotoa alba,* until it becomes bloated and dies. The bacteria carcasses fall to the bottom of the pond whereat the sulfur collects. The sulfur can be peridically harvested from the pond by scraping up and removing this bottom sulfur containing layer.

The various bacteria described herein are generally available at commercial bacteria supply houses. Only sufficient bacteria need be obtained from an outside source to initiate, that is, treat or innoculate, same into the pond, as the bacteria will rapidly multiply in the presence of suitable growth conditions therein. The bacteria of the present embodiment may also be found in most fresh water ponds and lakes, wherefrom they may be isolated and cultured. These bacteria may also be stored under freezing as a backup supply in case some catastrophe would destroy all of the bacteria in the pond.

After the scrubber effluent is regenerated in the basin or pond, the resultant solution is recycled to the scrubber and reused therein to remove sulfur dioxide from the stack gas. By the term regeneration is meant that sulfate radicals (or other reducible sulfur containing compounds) in the scrubber effluent are converted by previously described processes to hydrogen sulfide and oxide radicals. The oxide radicals (normally metallic oxides and according to the present embodiment magnesium oxides) are eventually converted to carbonates by reaction with carbon dioxide for reuse in the scrubber and thus form the regenerated scrubber solution. At the same time the hydrogen sulfide is converted to a non-gaseous and non-noxious form, preferably elemental sulfur, and is thereby removed from the regenerated scrubber solution and not allowed to escape into the air. It should be noted that the regenerated scrubber solution may contain fractions of various sulfates which have not yet been regenerated, bacteria, and other material normally found in the pond without harm to the process. These "extra" materials in the scrubber solution simply recycle back to the pond with the rest of the scrubber effluent.

EXAMPLES OF THE INVENTION

The examples which follow serve to illustrate the use of the present invention in regenerating fossil fuel power plant scrubber effluent. These examples are offered only to show the effect of the present invention on various scrubber solutions and are not meant to limit the invention thereto.

EXAMPLE I

A solution having about forty grams of magnesium sulfate is dissolved therein per liter of water, and being typical of certain fossil fuel power plant scrubber effluents, was placed in an open basin at approximately 32° Centigrade (C.) and treated or innoculated with *Desulfovibrio desulfuricans* and *Beggiatoa alba* bacteria. The bacteria grew in lower and upper strata respectively. The solution also had dissolved therein carbon dioxide and oxygen. Daily tests were performed for detection of a sulfate ion and carbonate ion. The carbonate ion appeared after about 3 days. The sulfate ion disappeared after about 30 days which represented regeneration of the solution into a state totally reuseable in a scrubber. (It should be noted that complete regeneration such as preformed herein is not necessary, since partially regenerated scrubber effluent will function in the scrubber). At no time was the presence of hydrogen sulfide detectable in the air above the basin.

EXAMPLE II

The same tests were preformed as in Example I except that the solution contained sodium sulfate. The results of these tests were essentially the same as Example I.

EXAMPLE III

The same tests were preformed as in Example I except that the solution contained calcium sulfate. Although some problems were encountered in keeping the calcium sulfate in solution without upsetting the bacteria in the respective strata, the results were essentially the same as Example I.

It is to be understood that while certain embodiments of my invention have been described herein, it is not to be limited to the specific forms herein described.

What is claimed and desired to secure by Letters Patent is:

1. A process for scrubbing sulfur dioxide from stack gas of fossil fuel burning including the steps of:
   (a) passing said stack gas through a scrubber vessel;
   (b) injecting a solution into said scrubber vessel contemporaneously with said stack gas; said solution having chemical reactants therein; said chemical reactants substantially reacting with said sulfur dioxide and forming inorganic, non-gaseous, and reducible sulfur containing compounds therewith; said reducible sulfur containing compounds being ejected from said scrubber in a liquid effluent thereby removing said sulfur dioxide from said stack gas;
   (c) treating said reducible sulfur containing compounds with a sulfur reducing microorganism, whereby hydrogen sulfide is produced in said effluent and said chemical reactants are regenerated;
   (d) treating said effluent having said hydrogen sulfide therein with a sulfur oxidizing microorganism whereby said hydrogen sulfide is converted to a non-noxious and non-gaseous sulfur containing compound; and
   (d) returning said regenerated chemical reactants to said scrubber vessel for reuse therein.

2. The process according to claim 1 wherein:
   (a) said chemical reactants are chosen from the group consisting of calcium carbonate, calcium oxide, magnesium carbonate, magnesium oxide, sodium carbonate, sodium oxide, and mixtures thereof;
   (b) said sulfur reducing microorganism is a bacteria chosen from the genus Desulfovibrio; and
   (c) said sulfur oxidizing microorganism is a bacteria chosen from the genus Beggiatoa.

3. The process according to claim 1 wherein:
   (a) said chemical reactants are comprised of magnesium carbonate;
   (b) said sulfur reducing microorganism is Desulfovibrio desulfuricans; and
   (c) said sulfur oxidizing microorganism is Beggiatoa alba.

4. In a process for scrubbing sulfur dioxide from stack gasses of a plant for burning fossil fuel containing sulfur, wherein metallic carbonates are converted to metallic sulfates in a scrubber and said metallic sulfates are then ejected from said scrubber in a liquid effluent, said stack gases and said effluent including carbon dioxide, the improvement comprising the regeneration of said metallic carbonates to a state suitable for reuse by said scrubber by the steps of:
   (a) placing said metallic sulfate containing effluent into a basin;
   (b) inoculating said effluent with a first bacteria from the genus Desulfovibrio selected from the species consisting of *desulfuricans, vulgaris, salexigens, africanus, gigas,* and compatible combinations thereof, whereby said metallic sulfates are converted to products including hydrogen sulfide and metallic oxides by said first bacteria; said metallic oxides reacting with said carbon dioxide thereby regenerating metallic carbonates;
   (c) inoculating said solution with a second bacteria from the genus Beggiatoa selected from the species consisting of *alba, arachnoida, gigantea, leptomitiformis, minima, mirablis,* and compatible combinations thereof, whereby elemental sulfur is produced from said hydrogen sulfide by said second bacteria;
   (d) removing said elemental sulfur from said solution; and
   (e) recirculating said solution with said regenerated metallic carbonates therein to said scrubber.

5. The process according to claim 4 wherein:
(a) said first bacteria is *Desulfovibrio desulfuricans*;
(b) said second bacteria is *Beggiatoa alba*; and
(c) said first and second bacteria are maintained substantially in lower and upper strata respectively of said effluent in said basin.

6. The process according to claim 5 wherein:
(a) said metallic carbonates are chosen from the group consisting of calcium carbonate, sodium carbonate, magnesium carbonate, and mixtures thereof.

7. The process according to claim 5 wherein:
(a) said metallic carbonates are substantially magnesium carbonate.

8. A process for producing elemental sulfur from sulfate radicals comprising:
(a) forming a solution of sulfate radicals from soluble stack gas components of fossil fuel; said solution having a lower stratum and an upper stratum associated therewith;
(b) exposing said solution in said lower stratum to a first bacteria from the genus Desulfovibrio selected from the species consisting of *desulfuricans, vulgaris, salexigens, africans, gigas*, and compatible combinations thereof; whereby hydrogen sulfide is produced by said first bacteria from said sulfate radicals; and
(c) exposing said solution in said upper stratum to a second bacteria from the genus Beggiatoa selected from the species consisting of *alba, arachnoida, gigantea, leptomitiformis, minima, mirablis*, and compatible combinations thereof; whereby said elemental sulfur is produced from said hydrogen sulfide by said second bacteria.

9. The process according to claim 8 wherein:
(a) said first bacteria is Desulfovibrio desulfuricans;
(b) said second bacteria is Beggiatoa alba; and wherein
(c) said upper stratum contains free oxygen for support of said second bacteria.

* * * * *